United States Patent [19]

Jackson

[11] Patent Number: 4,476,879
[45] Date of Patent: Oct. 16, 1984

[54] APPARATUS FOR AND METHODS OF COLLECTING URINE FROM LABORATORY ANIMALS

[76] Inventor: André J. Jackson, 3978 Woodhue Pl., Alexandria, Va. 22309

[21] Appl. No.: 314,776

[22] Filed: Oct. 26, 1981

[51] Int. Cl.³ .............................................. A61B 5/00
[52] U.S. Cl. .................... 128/760; 604/327; 604/352; 119/17
[58] Field of Search ............... 604/327, 346, 347, 348, 604/349, 351, 352, 354, 324, 326, 331, 332, 338; 128/760, 761, 765; 119/17

[56] References Cited

U.S. PATENT DOCUMENTS

| Re. 29,319 | 7/1977 | Nordby et al. | 604/355 |
| 2,182,702 | 12/1939 | Previn | 604/331 |
| 2,548,149 | 4/1951 | Fowler, Jr. | 604/347 |
| 3,077,883 | 2/1963 | Hill | 604/347 |
| 3,340,876 | 9/1967 | Hill | 604/347 |
| 3,698,360 | 10/1972 | Rubricius | 119/17 |
| 3,711,871 | 12/1973 | Sherin | 128/760 |
| 3,777,739 | 12/1973 | Raitto | 128/760 |
| 3,811,136 | 5/1974 | Whitney et al. | 128/761 |
| 3,881,465 | 5/1975 | Raitto | 128/760 |
| 4,020,843 | 5/1977 | Kanall | 604/351 |
| 4,202,057 | 5/1980 | Ibarra | 128/761 |

OTHER PUBLICATIONS

Carton et al., "Plastic Adhesive Method of Small Blood Vessel Surgery", World Neurology vol. 1, (361) pp. 356-361 (9-1960).
Leonard et al., "A Spray Gun For Tissue Adhesive", Surgery, vol. 57 #5, pp. 749-750 (5-1965).

Primary Examiner—Richard J. Apley
Assistant Examiner—Harry J. Macey
Attorney, Agent, or Firm—Quaintance & Murphy

[57] ABSTRACT

An apparatus for collecting urine from laboratory animals includes a collector for accumulating the urine and a mounting plate which is adhered to the abdomen of the animal with a quick-drying adhesive. Preferably, the collector is releaseably connected to the mounting plate by screw threads. When the collector is not being utilized, a gnaw-resistant protective block is mounted over the mounting plate to protect the mounting plate from gnawing by the rat.

The process for practicing the instant invention includes the steps of adhering the mounting plate 14 to the animal's abdomen with an adhesive applied so as to effect a seal around the opening of the animal's urethra in order to prevent contamination of the urine. Thereafter, the container is coupled to the mounting plate and urine collected. Urine may be drained from the collector with a hypodermic needle while the container is secured to the animal with the mounting plate or may be drained from the collector after the container has been removed from the animal.

17 Claims, 6 Drawing Figures

U.S. Patent    Oct. 16, 1984    4,476,879
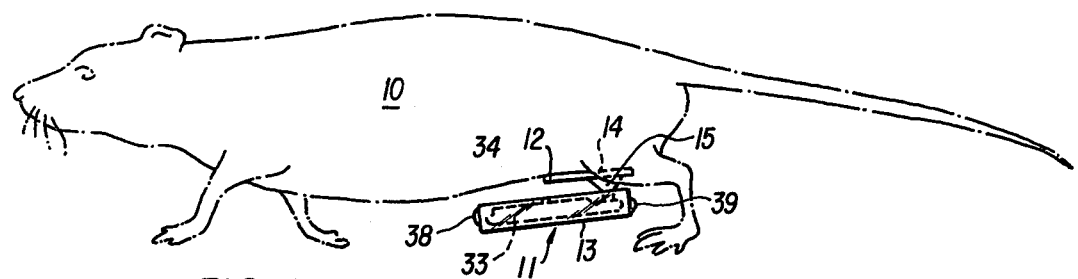
FIG. 1
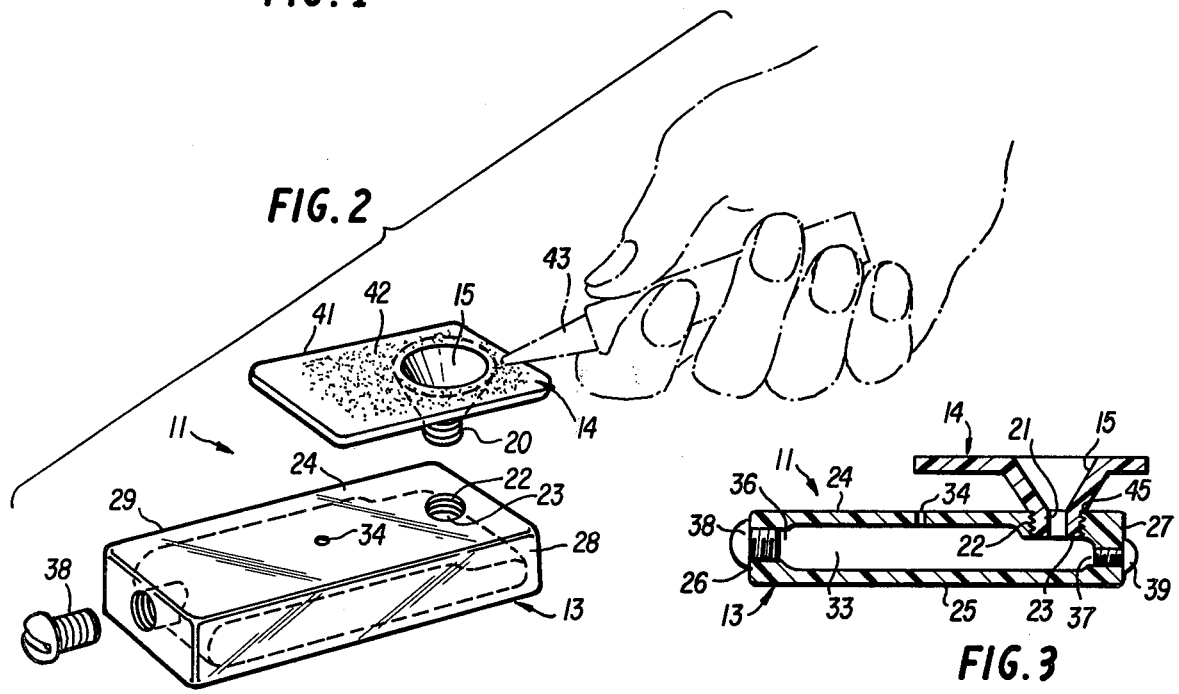
FIG. 2
FIG. 3
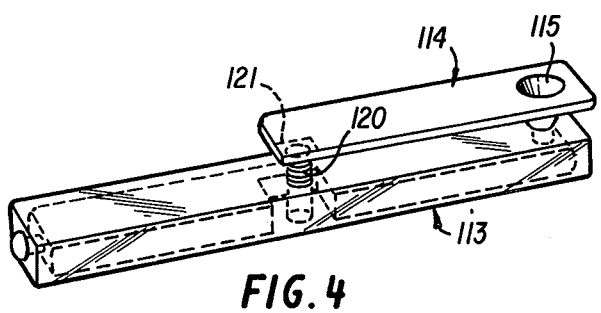
FIG. 4
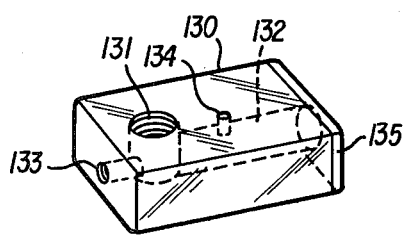
FIG. 5
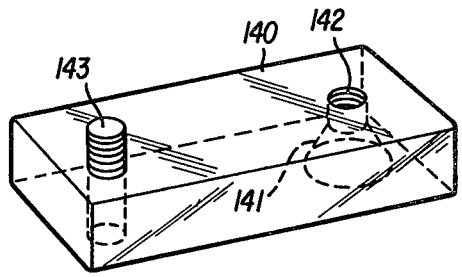

APPARATUS FOR AND METHODS OF COLLECTING URINE FROM LABORATORY ANIMALS

BACKGROUND OF THE INVENTION

1. Field of the Invention

The instant invention relates to apparatus for and methods of collecting urine from laboratory animals, and more particularly, the instant invention relates to apparatus for and methods of collecting urine from laboratory rodents in accordance with structures and procedures which prevent the urine from being contaminated by other substances present in the environment of the laboratory rodents.

2. Technical Considerations and Prior Art

In conducting experiments utilizing animals, it is frequently necessary to collect urine from the animals for analysis. For example, it is necessary to analyze the animal's urine when conducting bioavailability studies to determine if a drug ingested by a laboratory animal is absorbed, and when conducting toxicity studies to determine if there is any change in pH, excreted electrolites, etc. Moreover, is is frequently necessary to quantitatively collect and separate urine containing pharmaceuticals and their metabolites from fecal pharmaceuticals and metabolites and/or contaminants. Rats and mice are the primary laboratory animals utilized for bioavailability and toxicity studies. Since rats and mice are relatively small animals, collecting their urine while not drastically interfering with other body functions, such as their freedom of movement, has been a difficult task. The general approach is to simply place the animals in a cage with a screen floor which serves, in essence, as a filter that stops the animal's feces while allowing urine to flow through by gravity for collection in a container beneath the cage. This method is not entirely satisfactory because the urine can become contaminated as it flows over the feces or can become contaminated by food and food particles which drop on and through the screen. When testing pharmaceuticals in small rodents, the pharmaceuticals are normally administered via the food so that any food which is dropped on the screen floor by the animal can contaminate the animal's urine with unconsumed pharmaceutical as the urine washes over the food. This would indicate that a portion of the pharmaceutical had been adsorbed into the animal's body from ingestion of the food when, in fact, it had not. None of the procedures proposed or practiced prior to the instant invention prevents this contamination. Moreover, the urine collectors currently utilized have metal in direct contact with the animal which may lead to undesirable oxidation of urinary pharmaceuticals and metabolites.

SUMMARY OF THE INVENTION

It is a feature of the instant invention to provide new and improved apparatus for and methods of collecting urine from animals wherein the urine is not contaminated by the animal's food or feces.

In view of this feature, the instant invention contemplates a container having a chamber therein for accumulating urine as the urine is passed. There is an opening through the container wall which is registered with an opening through a mounting surface. The mounting surface is adhered to the abdomen of the animal with the openings therein and in the container aligned with the animal's urethra. Adhesion between the mounting surface and the animal's abdomen is accomplished by a quick-drying cement which seals the area around the opening to the animal's abdomen, as well as holding the apparatus in place.

The process in accordance with the instant invention contemplates the steps of adhering a Teflon, i.e. poly(tetrafluoroethylene), mounting plate with an opening therethrough to the abdomen of a laboratory animal with the opening in communication with the urethra of the laboratory animal. This is done by spreading a layer of adhesive between the animal's abdomen and the Teflon, i.e. poly(tetrafluoroethylene), mounting plate in an area which surrounds the opening through the mounting plate. Consequently, the opening is unobstructed but sealed. Thereafter, a container with a chamber therein having an opening therethrough in communication with the chamber is attached to the mounting plate with the openings registered with one another so that urine flows through the openings and is collected in the chamber. The urine which has accumulated in the chamber is then drained from the chamber. The process further contemplates removing the container from the mounting plate either prior to or after draining the urine and the step of mounting a gnaw-proof block having a hole completely therethrough over the Teflon, i.e. poly(tetrafluoroethylene), mounting plate with the hole aligned with the hole in the mounting plate so that the animal can freely pass urine when it is not desired to collect urine, while the mounting plate is protected from gnawing by the animal.

BRIEF DESCRIPTION OF THE DRAWINGS

FIG. 1 is a perspective side view showing a rat sporting his new and improved urine collector, with portions of the urine collector shown in phantom.

FIG. 2 is a perspective, exploded view of the urine collector shown in FIG. 1 with portions shown in phantom.

FIG. 3 is a cross-section through the urine collector of FIGS. 1 and 2.

FIG. 4 is a perspective view of another embodiment of the urine collector, having an increased collection capacity and having a set screw utilized therewith for alignment of separate container and mounting plate portions of the collector.

FIG. 5 is a perspective view, with portions in phantom, showing a third embodiment of the urine collector for use with relatively small rodents, such as mice.

FIG. 6 is a perspective view of a solid, gnaw-proof block which is utilized with a mounting plate shown in FIGS. 1-4 when a container is not attached to the mounting plate.

DESCRIPTION OF THE PREFERRED EMBODIMENTS

Referring now to FIG. 1, there is shown a rat 10 with the urine collecting apparatus, designated generally by the numeral 11, of the instant invention adhered to its abdomen 12. Although the urine collection apparatus 11 may be used with male or female rats, the rats utilized thus far in bioavailability and toxicity studies have been male rats. The collection apparatus 11 includes a container 13 and a mounting plate 14. The mounting plate 14 has a projecting funnel 15 which receives the rat's penis (not shown). The mounting plate 14 is adhered to the rat's abdomen 12 by a quick-drying cyanoacrylate adhesive, such as "Eastman 910". This type of adhesive is, apparently, not irritating to the rat and, as far as is known, is neither abosorbed through its skin nor toxic.

Preferably, the mounting plate 14 is made from Teflon, i.e. poly(tetrafluoroethylene), because Teflon, i.e. poly(tetrafluoroethylene), is somewhat flexible and is non-irritating. However, Teflon, i.e. poly(tetrafluoroethylene), is also relatively soft and can be gnawed by rats, mice and other rodents. In order to prevent this, the container 13 is made from a relatively hard plastic material, for example, which overlies the mounting plate 14 so as to shield the mounting plate from gnawing by the rat. Preferably, the container 13 is transparent so that an observer can tell when it is full or when a sufficient quantity of urine has been collected.

Referring now to FIGS. 2 and 3 where the structure of the urine collector 11 is shown in more detail, it is seen that the container 13 and mounting plate 14 are separate parts joined by first screw threads 20 disposed around a cylindrical projection or annulus 21 at the mouth of the funnel 15. The screw threads 20 couple with second screw threads 22 in an opening 23 through the top wall 24 of the container 13. The top wall 24 cooperates with a bottom wall 25, end walls 26 and 27, and side walls 28 and 29 to define a chamber 33 in the container 13. The chamber 33 is vented by a vent 34 in top wall 24 of the container 13. In order to drain the container 13, one or more drains, such as the drains 36 and 37, are positioned in the end walls 26 and 27. The drains 36 and 37 are threaded and plugged with Teflon, i.e. poly(tetrafluoroethylene), screws 38 and 39. In order to withdraw urine from the chamber 33, a hypodermic needle is simply inserted in one of the drains and the urine pulled into the needle. It is desirable to have two drains 36 and 37 to facilitate cleaning of the chamber 33.

Referring now more specifically to the mounting plate 14, it is seen that the mounting plate 14 has a mounting surface or pad 41 to which a quick-drying adhesive 42 is applied from a conventional dispenser 43. The quick-drying adhesive surrounds the funnel 15, which funnel defines openings through the surface 41 and through the mounting plate 14 which openings allow urine to flow to the chamber 33 in the container 13. Since the adhesive 42 surrounds the opening, it also serves to seal the opening so that all of the urine flows into the container and so that the urine cannot become contaminated. Preferably, the funnel 15 is molded integrally with the mounting plate 14 and is, therefore, also made of Teflon, i.e. poly(tetrafluoroethylene). Since the threads 20 on the cylindrical projection 21 are made of Teflon, i.e. poly(tetrafluoroethylene), they can deform slightly as they are screwed into the hole 23 and mesh with the threads 22 on the housing 13, which threads 22 are relatively hard since the housing 13 is made of hard, gnaw-resistant plastic. Accordingly, a relatively tight seal can be effected between the funnel 15 and the top wall of the chamber 33. In order to have proper alignment between the container 13 and mounting plate 14, so that the longitudinal axis of the container and the longitudinal axis of the mounting plate are generally aligned, the funnel 15 has a shoulder 45 (see FIG. 3) which abuts the top wall 24 of the container 13 to stop rotation of the container relative to the mounting plate when the longitudinal axes are generally aligned.

Referring now to FIG. 4 where another embodiment of the instant invention is shown, an elongated urine container 113 is connected to a relatively elongated, Teflon, i.e. poly(tetrafluoroethylene), mounting plate 114 by a funnel 115 in generally the same manner as the container 13 is connected to the mounting plate 14 by the funnel 15 in FIGS. 1-3. This arrangement is utilized for larger rodents, such as relatively large rats, which naturally have a greater urine output and require a larger container. In this embodiment, a set screw 120 is utilized as a detent to keep the longitudinal axes of the urine container 113 and mounting plate 114 aligned. The set screw 120 is advanced to seat in an indentation 121 formed in the bottom surface of the mounting plate 114. When the screw 120 is advanced to seat relatively tightly in the indentation 121, the container 113 cannot rotate about the axis of funnel 115. Consequently, the rat cannot urge the container 113 aside and gnaw on the relatively soft Teflon, i.e. poly(tetrafluoroethylene), mounting plate 114. When it is desired to remove the container 113, the screw 120 is backed off and the container 113 rotated to unscrew from the funnel 115.

Referring now to FIG. 5, there is shown still another embodiment of the instant invention wherein a relatively small container 130 is formed from a single block of plastic by a series of intersecting bores. A chamber 132 for containing the urine is formed by axially boring a relatively large bore in the block of material; a drain 133 is formed by a second smaller longitudinal bore which is threaded to receive a screw-type plug, such as the screw 38 shown in FIG. 2; a lateral bore 134 forms a vent; and a second relatively large threaded lateral bore 131 receives the threaded end 20 of a funnel, such as the funnel 15 shown in FIGS. 1-3. The bore 132 which forms the chamber may be sealed by simply adhering a plate 135 over the end of the block 130.

When a sample is not being collected from a rat and the container 13 is not attached, it is still necessary to protect the mounting plate 14. This is accomplished by screwing a gnaw-resistant block 140 to the threads 20 of the funnel 15. The gnaw-resistant block has a flared funnel 141 with a cylindrical top portion 142 that is threaded with third screw threads to receive the threads 20 on the funnel 15 (shown in FIG. 2). In order to keep the block 140 from turning relative to the mounting plate 14, the block may have a set screw 143 thereon which seats in a slot 121 in the mounting plate. When the block is mounted in place, the rat's urine simply flows out of the funnel 141 and the rat's urinary function is not interrupted. Utilization of a block, such as the block 140, protects the mounting plate 114 while avoiding urine collections which are neither necessary nor needed.

The foregoing examples and embodiments are merely illustrative of the invention, which is to be limited only by the following claims.

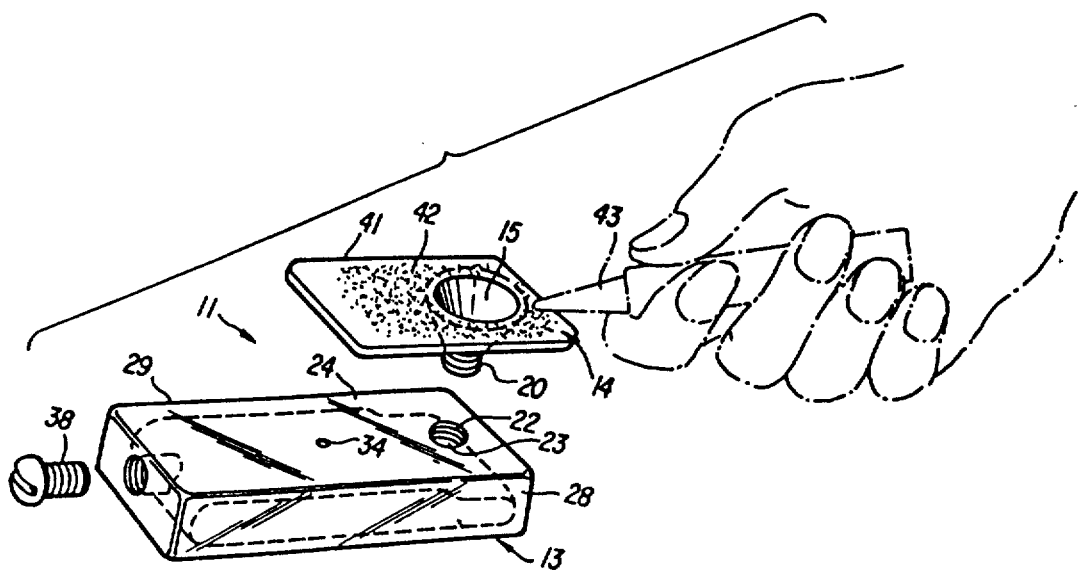

What is claimed is:

1. A process for collecting urine from a laboratory animal comprising the steps of:
permanently adhering a non-metallic mounting plate having a length and width defining a first perimeter defining a first area with an opening therethrough to the abdomen of the laboratory animal with the opening in communication with the urethra of the laboratory animal by spreading a layer of adhesive between the animal's abdomen and the mounting plate in an area which surrounds the opening through the mounting plate to leave the opening unobstructed but sealed;
connecting to the mounting plate a container of hard gnaw-resistant material, having a chamber therein and an opening therethrough in communication with the chamber; the container having a length and width defining a second perimeter defining a second area substantially parallel to and at least as large as said first area wherein the first area does not extend beyond the perimeter defined by the second area; the connection being effected by connecting the openings in the mounting plate and container to one another so that the container overlaps and shields the mounting plate from gnawing by the animal and so that urine flows into the chamber as the urine is passed, and draining accumulated urine from the container.

2. The process of claim 1 further comprising the step of removing the container from the mounting plate while leaving the mounting plate adhered in place.

3. The process of claim 1 or 2 further including the steps of disconnecting the container when the container is not needed and connecting a gnaw-resistant block with a hole therethrough to the connecting plate, the hole through the block registering with the opening through the mounting plate.

4. An apparatus for collecting urine from a laboratory animal, the apparatus comprising:

a container of a selected length and width defining a perimeter enclosing a selected area, the container having a chamber for accumulating urine as the urine is passed, the container including a top wall having an opening therethrough and being made of a hard gnaw-resistant material;

a mounting plate for mounting the container on the abdomen of the animal, the mounting plate having a length and width defining a perimeter enclosing an area no greater than, substantially parallel to and within a perimeter defined by the area of said top wall of the container; the plate having an opening therethrough which opening is aligned generally with the animal's urethra, and the plate having a first surface for abutting the abdomen of the animal;

a layer of permanent adhesive on the first surface for securing the plate to the abdomen of the animal;

a coupling having first and second parts, the first part being attached to the mounting plate; the second part being attached to the container and being positioned at a location spaced from the perimeter of the container a sufficient distance to position the container in substantial overlapping relationship with the mounting plate upon connecting the coupling, whereby the hard container shields the mounting plate, preventing the animal from chewing the mounting plate, and whereby the container can be detached from the mounting plate for emptying.

5. The apparatus of claim 4 wherein the first part of the coupling is aligned with the opening through the mounting plate and the second part of the coupling is aligned with the opening through the top wall of the container.

6. The apparatus of claim 5 wherein the first coupling part and second coupling part both include screw threads which compliment one another.

7. The apparatus of claim 6 wherein the screw threads of the first coupling are adjacent to the free end of a hollow projection extending from the mounting plate and wherein the screw threads terminate before reaching the mounting plate.

8. The apparatus of claim 7 wherein the hollow projection has a converging inner wall which is funnel-shaped.

9. The apparatus of claim 8 wherein the threads of the first coupling part are external and those of the second coupling part are internal wherein the first coupling part is received within the second coupling part.

10. The apparatus of claim 9 wherein there is a vent hole in the top surface of the container.

11. The apparatus of claim 10 wherein there is an outlet in one end of the container for emptying the container and a plug for closing the outlet while urine is being collected.

12. The apparatus of claim 11 wherein there is an opening in the other end of the container to facilitate cleaning the container and a plug for closing the opening.

13. The apparatus of claim 6 further including detent means extending between the mounting plate and container for preventing rotation of the container with respect to the mounting plate.

14. The apparatus of claim 4 wherein the apparatus further includes a block without a collection chamber therein for use when the container is not mounted on the mounting means; the block having a perimeter defining an area at least as large as that of the mounting plate; the block having a third coupling part, similar to the second coupling part on the container and connectable to the first coupling part on the mounting plate when the container is not coupled thereto; the block having a hole extending completely therethrough aligned with the third coupling part to permit urine to pass through the block, the third coupling part and the hole being positioned at a location spaced from the perimeter of the protective block a sufficient distance to position the protective block in substantial overlapping relationship with the mounting plate upon connecting the third coupling part to the first coupling part whereby the protective block shields the mounting plate when coupled thereto.

15. The apparatus of claim 4 wherein the coupling means includes means for spacing the container from the mounting plate.

16. The apparatus of claim 15 wherein the spacing means comprises a hollow projection extending from the mounting plate toward a free end, the hollow projection having a converging inner wall which is funnel-shaped.

17. The apparatus of claim 16 wherein the coupling means includes a threaded portion adjacent the free end of the hollow projection and internal threads in the container which mate with the threaded portion to couple the container to the hollow projection.

* * * * *

UNITED STATES PATENT AND TRADEMARK OFFICE
CERTIFICATE OF CORRECTION

PATENT NO. : 4,476,879

DATED : Oct. 16, 1984

INVENTOR(S) : Andre J. Jackson

It is certified that error appears in the above-identified patent and that said Letters Patent is hereby corrected as shown below:

The title page showing the illustrative figure should be deleted to appear as per attached title page.

Non-identified figure in the issued Patent should be labelled as Fig. 6.

Signed and Sealed this

Twenty-fifth Day of June 1985

[SEAL]

*Attest:*

DONALD J. QUIGG

*Attesting Officer*     *Acting Commissioner of Patents and Trademarks*

United States Patent [19]

Jackson

[11] Patent Number: 4,476,879
[45] Date of Patent: Oct. 16, 1984

[54] APPARATUS FOR AND METHODS OF COLLECTING URINE FROM LABORATORY ANIMALS

[76] Inventor: André J. Jackson, 3978 Woodhue Pl., Alexandria, Va. 22309

[21] Appl. No.: 314,776

[22] Filed: Oct. 26, 1981

[51] Int. Cl.³ .............................................. A61B 5/00
[52] U.S. Cl. ................................... 128/760; 604/327; 604/352; 119/17
[58] Field of Search ............... 604/327, 346, 347, 348, 604/349, 351, 352, 354, 324, 326, 331, 332, 338; 128/760, 761, 765; 119/17

[56] References Cited

U.S. PATENT DOCUMENTS

| Re. 29,319 | 7/1977 | Nordby et al. | 604/355 |
|---|---|---|---|
| 2,182,702 | 12/1939 | Previn | 604/381 |
| 2,548,149 | 4/1951 | Fowler, Jr. | 604/347 |
| 3,077,883 | 2/1963 | Hill | 604/347 |
| 3,340,876 | 9/1967 | Hill | 604/347 |
| 3,698,360 | 10/1972 | Rubricius | 119/17 |
| 3,711,871 | 12/1973 | Sherin | 128/760 |
| 3,777,739 | 12/1973 | Raitto | 128/760 |
| 3,811,136 | 5/1974 | Whitney et al. | 128/761 |
| 3,881,465 | 5/1975 | Raitto | 128/760 |
| 4,020,843 | 5/1977 | Kanall | 604/351 |
| 4,202,057 | 5/1980 | Ibarra | 128/761 |

OTHER PUBLICATIONS

Carton et al., "Plastic Adhesive Method of Small Blood Vessel Surgery", World Neurology vol. 1, (361) pp. 356-361 (9-1960).
Leonard et al., "A Spray Gun For Tissue Adhesive", Surgery, vol. 57 #5, pp. 749-750 (5-1965).

Primary Examiner—Richard J. Apley
Assistant Examiner—Harry J. Macey
Attorney, Agent, or Firm—Quaintance & Murphy

[57] ABSTRACT

An apparatus for collecting urine from laboratory animals includes a collector for accumulating the urine and a mounting plate which is adhered to the abdomen of the animal with a quick-drying adhesive. Preferably, the collector is releaseably connected to the mounting plate by screw threads. When the collector is not being utilized, a gnaw-resistant protective block is mounted over the mounting plate to protect the mounting plate from gnawing by the rat.

The process for practicing the instant invention includes the steps of adhering the mounting plate 14 to the animal's abdomen with an adhesive applied so as to effect a seal around the opening of the animal's urethra in order to prevent contamination of the urine. Thereafter, the container is coupled to the mounting plate and urine collected. Urine may be drained from the collector with a hypodermic needle while the container is secured to the animal with the mounting plate or may be drained from the collector after the container has been removed from the animal.

17 Claims, 6 Drawing Figures